(12) United States Patent
Joeris (10) Patent No.: US 8,117,924 B2
(45) Date of Patent: Feb. 21, 2012

(54) APPARATUS, SYSTEM, AND METHOD FOR IN-SITU MEASUREMENTS

(75) Inventor: Klaus Michael Joeris, Sindelsdorf (DE)

(73) Assignee: Bayer Healthcare LLC, Tarrytown, NY (US)

( * ) Notice: Subject to any disclaimer, the term of this patent is extended or adjusted under 35 U.S.C. 154(b) by 573 days.

(21) Appl. No.: 12/226,591

(22) PCT Filed: Apr. 23, 2007

(86) PCT No.: PCT/US2007/009883
§ 371 (c)(1),
(2), (4) Date: May 28, 2009

(87) PCT Pub. No.: WO2007/124159
PCT Pub. Date: Nov. 1, 2007

(65) Prior Publication Data
US 2009/0305393 A1    Dec. 10, 2009

Related U.S. Application Data

(60) Provisional application No. 60/794,269, filed on Apr. 21, 2006.

(51) Int. Cl.
*G01N 1/02* (2006.01)

(52) U.S. Cl. ... 73/863; 73/64.56; 73/863.84; 422/82.08; 435/287.1

(58) Field of Classification Search ............... 73/64.56, 73/863.84; 422/82.08; 435/287.1
See application file for complete search history.

(56) References Cited

U.S. PATENT DOCUMENTS

| | | | | |
|---|---|---|---|---|
| 6,809,862 | B2* | 10/2004 | Behnsen et al. | 359/392 |
| 7,384,783 | B2* | 6/2008 | Kunas et al. | 435/289.1 |
| 2006/0019385 | A1* | 1/2006 | Smith et al. | 435/348 |

OTHER PUBLICATIONS

Bioprocess Technology: Fermentation, Biocatalysis, Bioseperation, vol. 1-5, Michael C. Flickinger—University of Minnesota, St. Paul, Minnesota; Stephen W. Drew—Merck and Co., Inc. , Rahway, New Jersey. Copyright 1999 by John Wiley & Sons, Inc.*

* cited by examiner

*Primary Examiner* — Hezron E Williams
*Assistant Examiner* — Hoang Nguyen (57) ABSTRACT

The present invention relates to apparatus, systems and methods for performing in situ measurements, and, more particularly, to apparatus, systems and methods that can isolate a sample from a bulk fluid to measure characteristics of same without unwanted effects of perturbation in the bulk fluid.

34 Claims, 14 Drawing Sheets

APPARATUS, SYSTEM, AND METHOD FOR IN-SITU MEASUREMENTS

RELATED APPLICATIONS

This application is a national stage filing under 35 U.S.C. §371 of International Application No. PCT/US2007/009883, filed on Apr. 23, 2007, which claims the benefit of the filing date of U.S. Provisional Application No. 60/794,269, filed on Apr. 21, 2006. The teachings of the referenced Applications are incorporated herein by reference in their entirety. International Application No. PCT/US2007/009883 was published under PCT Article 21(2) in English.

BACKGROUND (a) Field

The present invention relates to apparatus, systems and methods for performing in situ measurements, and, more particularly, to apparatus, systems and methods that can isolate a sample from a bulk fluid to measure characteristics of same without unwanted effects of perturbation in the bulk fluid.

(b) Description of the Related Art

In situ measurement and the use of probes in implementing the same are subjects of much current interest due to their tremendous variety of applications. Whether it be for the monitoring of a cell culture, aquatic systems, or ecosystems, the accurate measurement of parameters in the system is useful for detecting natural, spatial, and/or temporal variations.

This type of undertaking is ideally performed in situ as the conventional approach of sample removal from the system, storage, and/or transport heightens the risk for contamination and inaccurate measurement of system conditions. In bioreactor processes, for instance, the ability to monitor cellular physiological states and system parameters is essential to control and maintain the system at desired conditions.

In the cell culture context, the tracking of metabolic states is very important for, e.g. designing feeding strategies, process scale-up, and calculation of optimal harvest time, etc. A commonly used indicator of metabolic activity in cells is the oxygen uptake rate or OUR.

One conventional method of measuring OUR, known as the dynamic method, requires stopping all gas supply then monitoring the oxygen consumption over time. This creates a harsh and significant disturbance to the cells, which consequently impacts cell proliferation, results in potentially erroneous readings, and does not allow for an extended period of continuous, real-time monitoring.

Figure 1A:
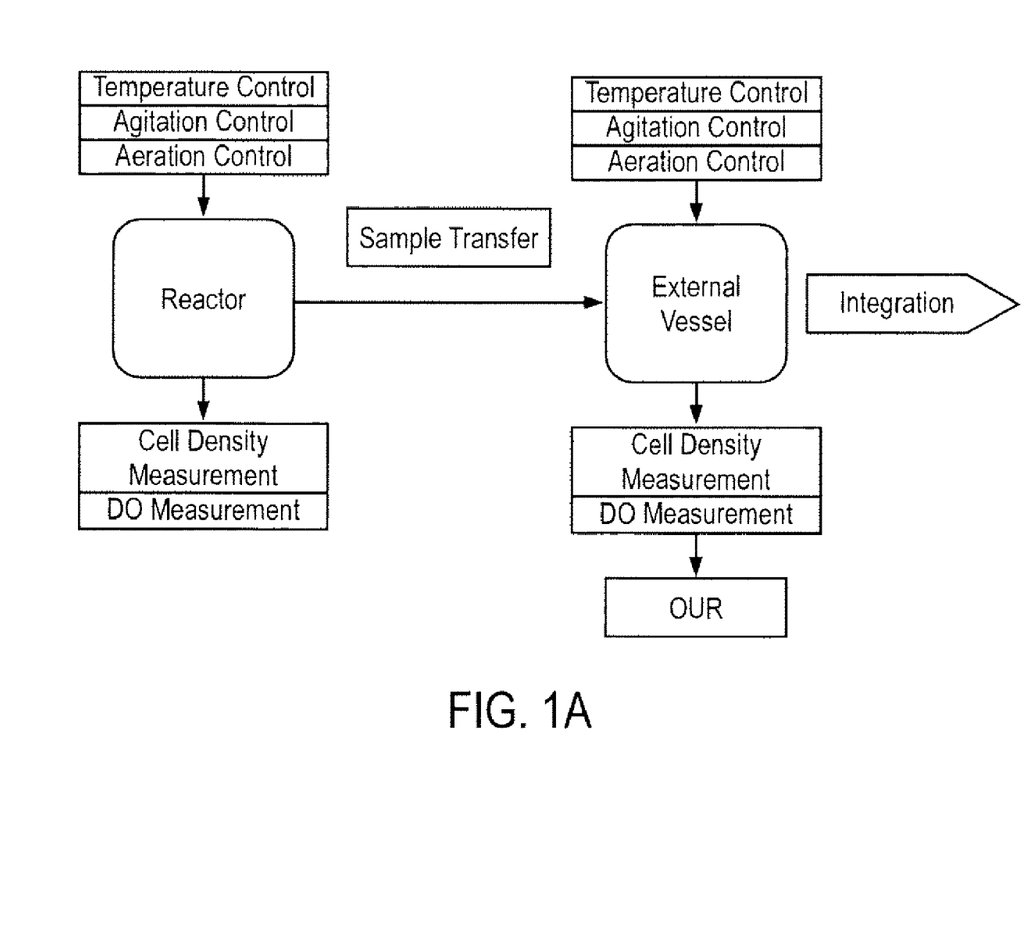
FIG. 1 provides conceptual views of a conventional method of measuring OUR, shown on the left as FIG. 1A, juxtaposed with an exemplary embodiment of the in situ method of the invention, shown on the right as FIG. 1B.

Another conventional method, illustrated in FIG. 1A, involves drawing a sample from the bioreactor and transferring it to an external vessel equipped with a monitoring and control system. Conditions, such as pH, temperature, aeration, etc., in the external vessel must be adjusted and controlled to mirror those of the bioreactor in order to obtain accurate and reliable readings. Duplicating these conditions, however, is challenging and time-consuming. In light of the above, apparatus and methods for in situ measurements that reduce the effects of system perturbations are highly desirable.

BRIEF SUMMARY OF THE INVENTION

According to one embodiment of the present invention, an apparatus for in situ measurements is disclosed having a body, a separator, a holder, and one or more probes. The body is configured for insertion into a bulk fluid and includes an interior and one or more apertures for fluid communication between the interior and the bulk fluid. The separator is received in the body interior and movable between an open position remote from the one or more apertures and a closed position adjacent to the one or more apertures. The holder, which is mounted within the separator, includes a chamber wall. The chamber wall, separator, and body interior together define a sample chamber. One or more probes are received by the holder with the end(s) extending into the sample chamber.

In another embodiment of the present invention, a system for in situ measurements comprises the aforementioned apparatus, a vessel containing the bulk fluid, and a retraction assembly mounted on the vessel.

In yet another embodiment of the invention, a method of performing in situ measurements is disclosed, which involves first contacting the body of the apparatus of the invention with the bulk fluid when the separator is in the open position then measuring one or more parameters of the bulk fluid using one or more probes.

In still another embodiment of the invention, the method of performing in situ measurements includes contacting the body of the apparatus of the invention with the bulk fluid when the separator is in the open position; isolating a sample of the bulk fluid within the sample chamber by moving the separator to the closed position; and measuring one or more parameters of the sample using one or more probes.

In another embodiment of the invention, the method of performing in situ measurements includes contacting the body of the apparatus in the system disclosed herein with the bulk fluid when the separator is in the open position and measuring one or more parameters of the bulk fluid using one or more probes.

In yet another embodiment of the present invention, the method of performing in situ measurements includes contacting the body of the apparatus in the system disclosed herein with the bulk fluid when the separator is in the open position; isolating a sample of the bulk fluid within the sample chamber by moving the separator to the closed position; and measuring one or more parameters of the bulk fluid using one or more probes.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIGS. 2A and 2C illustrate an exemplary embodiment of the present invention in exploded view and assembled view, respectively, whereas FIGS. 2B and 2D illustrate an exemplary embodiment of the present invention with a commercially available retraction housing in exploded view and assembled view, respectively.

FIG. 5 provides detailed schematic of an exemplary embodiment of the present invention.

FIG. 8 provides side cross-sectional views of an apparatus of the invention, whereas

DETAILED DESCRIPTION OF THE INVENTION

Reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims. While the invention will be described with reference to an apparatus having features suitable for use with cell culture, it will be appreciated that the apparatus and system can be used for in situ measurement of any fluid environment outside of the bioreactor context.

As used herein, the term "bulk fluid" refers to a volume of fluid from which a sample can be isolated and analyzed.

Embodiments described herein provide apparatus, systems, and methods for in situ measurements that isolate a sample of a bulk fluid, such as that in a reactor, aquatic system or ecosystem. Characteristics of the sample can then be measured without noise from perturbation of the bulk fluid.

Referring to FIG. 1A, which shows a conceptual view of conventional measurement of OUR, a sample of fluid in the reactor is typically removed from the system and transferred to an external vessel, where parameters such as OUR are measured. Other parameters that can be measured include, without limitation, nitrification rate, denitrification rate, etc. Conditions in the external vessel, such as temperature, agitation, and aeration, etc. must be precisely controlled to correspond to conditions in the reactor. As previously discussed, removal from the system presents various challenges and drawbacks. The present invention offers a solution by providing apparatus, systems, and methods for in situ measurement that obviate the need for removal and transfer to a separate controlled system. It achieves this by isolating a sample of the media or bulk fluid in a compartment within the reactor by means of an apparatus that will be described below. Because the sample fluid remains in the reactor, additional controls are not necessary. The apparatus of the invention can also be shifted to the closed position, which enables it to function as a conventional sensor, detecting parameters such as pH, temperature, dissolved oxygen, etc. and measuring changes in the reactor media.

Figure 2A:
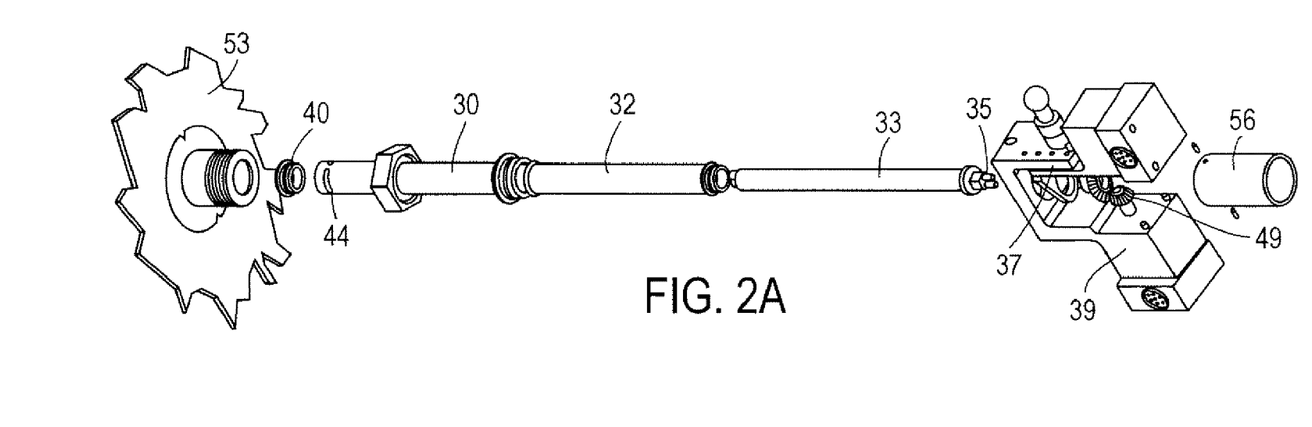
Figure 2B:
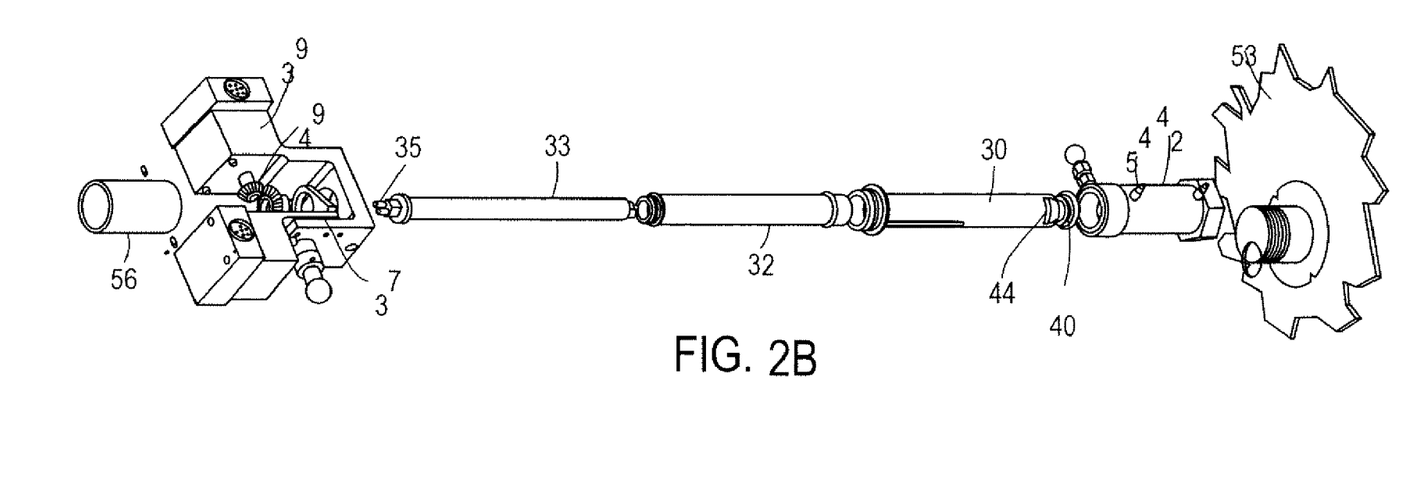
Figures 2C, 2D:
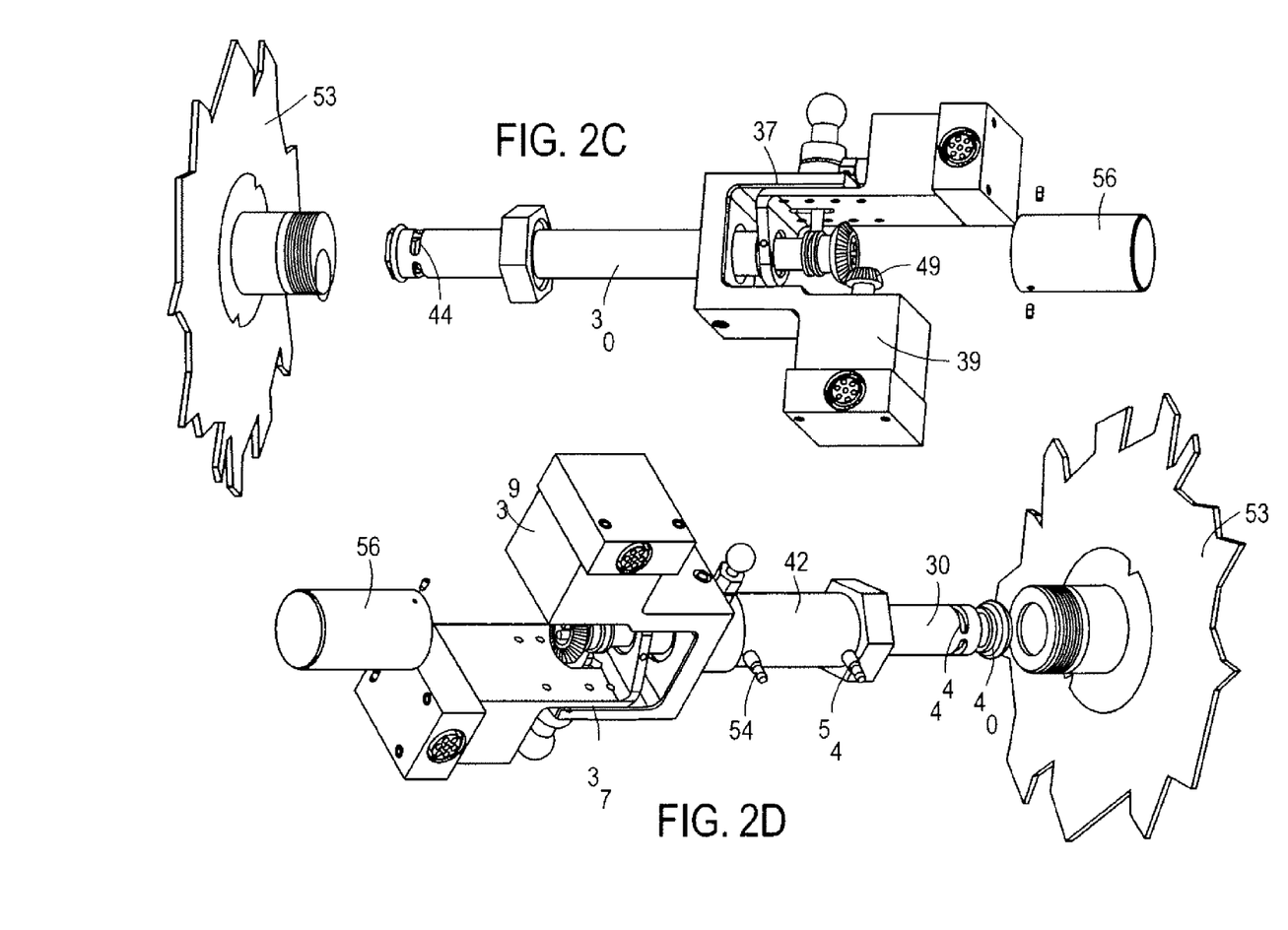

In exemplary embodiments, as shown in FIG. 2, an apparatus of the invention includes a body 30, a separator 32, a probe holder 33, and one or more probes 35. In some embodiments, the apparatus can further include a linear stage and actuator 37 which controls the separator movement, a stepper motor and gear box 39 that controls the holder movement, an end cap 40 that attaches to one end of the body, and/or a retraction housing 42. The body is configured with one or more apertures 44 that, when unobstructed, allow fluid communication between the interior of the housing and its surrounding environment. In the illustrated embodiment, the body includes three apertures, however, one will appreciate that one or more apertures of various geometries and dimensions may be used. The body, separator and holder may be constructed of a gas and/or liquid-impermeable material such as a metal, alloy, elastomer, plastic, polyurethane or composite. One will appreciate that these components may be constructed of any combination of these materials and/or other suitable materials. The body may be a single monolithically formed body or may comprise multiple parts fitted together, as exemplified in FIGS. 2B and 2D, showing a screw-on or otherwise removable end cap 40 at the distal end of body 30. While a body with a removable end cap 40 such as that shown in FIG. 2 may be easier to make for machining considerations than one that is formed integrally, the present invention is not limited to any particular construction and one will appreciate that the body and other components may have various configurations.

Figure 9:
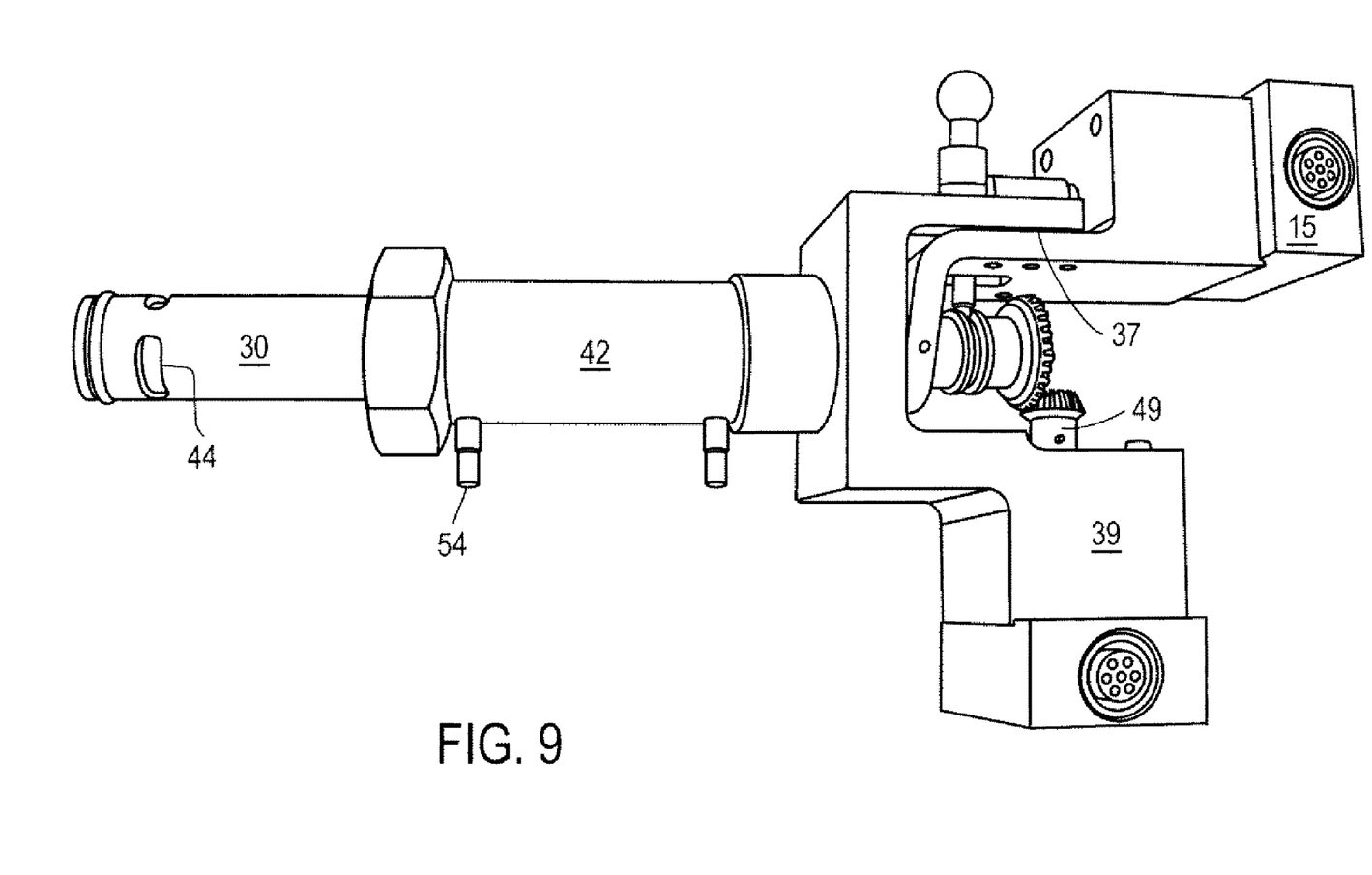
FIG. 9 is an external side view of an apparatus of the invention in the closed position.
Figure 10:
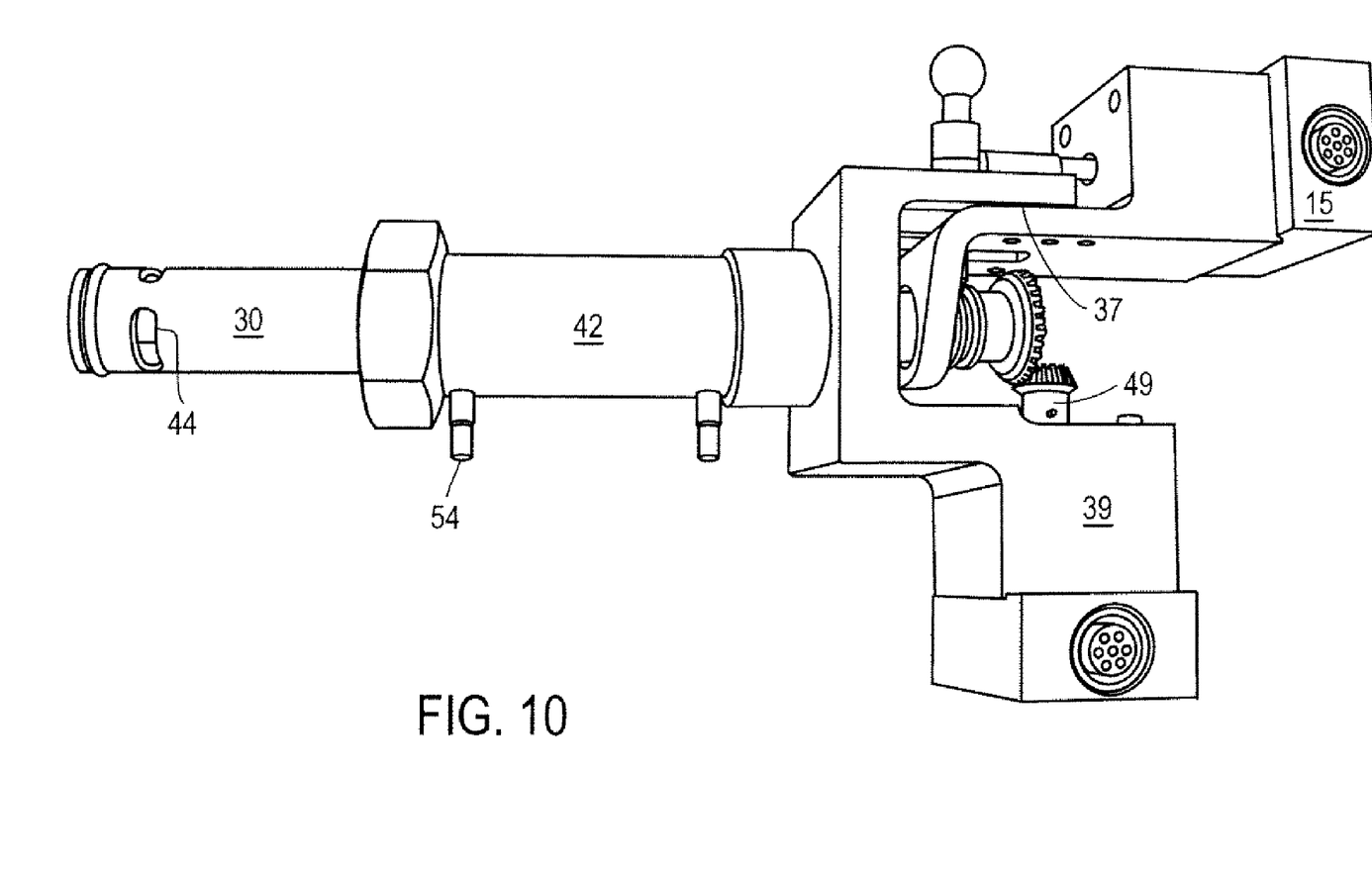
FIG. 10 is an external side view of an apparatus of the invention in open position.

Referring to FIG. 2-5, a separator 32 is provided in the interior of and movable within the body 30. In the illustrated embodiment, separator 32 moves axially between an open position, as shown in FIGS. 5B and 10, and a closed position, as shown in FIGS. 5C and 9. When the separator is in the open position, the body interior is in fluid communication with the bulk fluid, as illustrated by the arrow indicating fluid movement through the apertures 44. When the separator is in the closed position, the apertures are sealed such that the body interior is fluidly isolated from the bulk fluid, as illustrated by the curved arrow at the upper aperture in FIG. 5C.

Figure 1B:
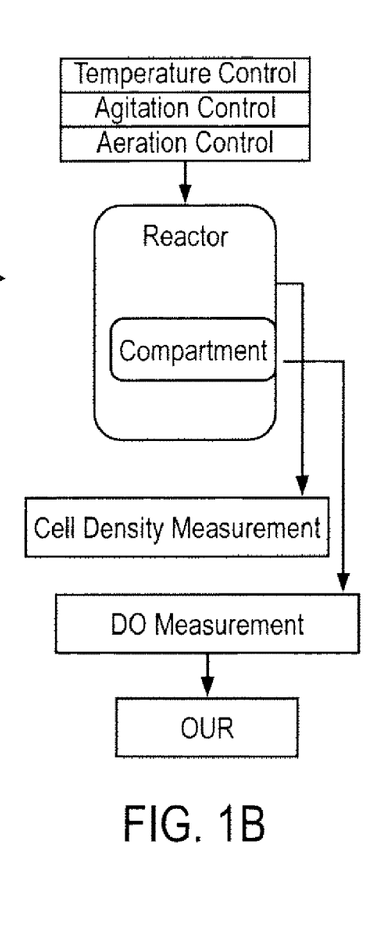
Figure 5A:
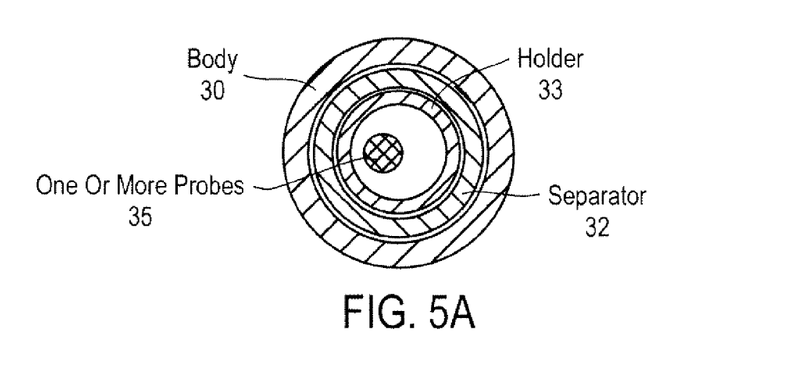
FIG. 5A is a front cross-sectional view whereas FIG. 5B and FIG. 5C side cross-sectional views of a sample chamber portion of the invention in open and closed position, respectively.
Figure 5B:
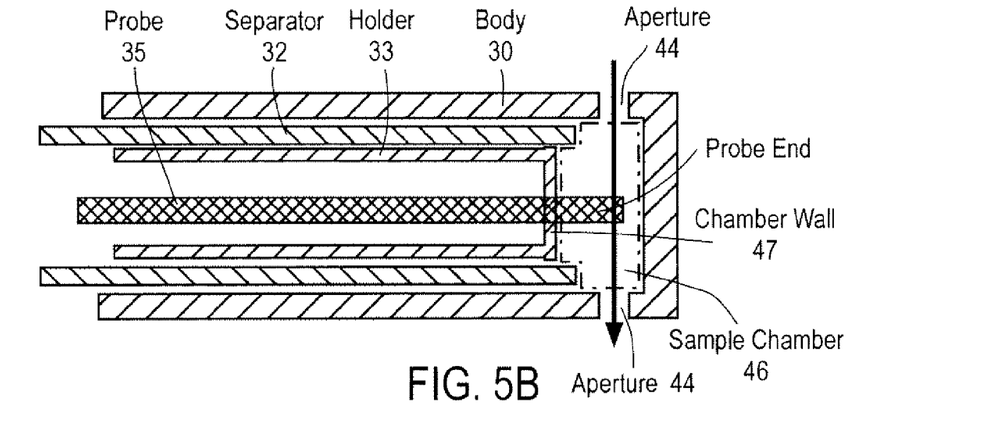
Figure 5C:
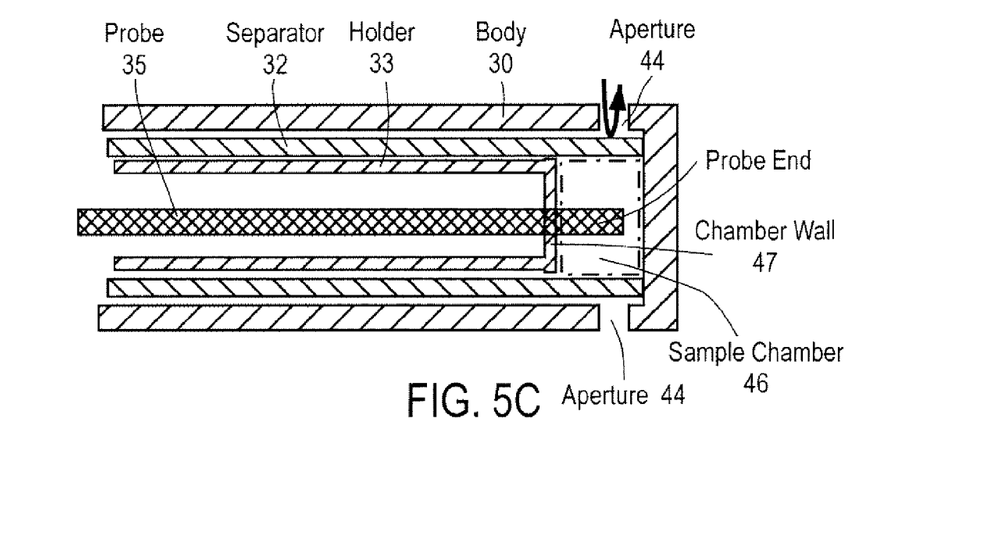

Therefore, in some embodiments, the apparatus has two modes or positions: an open mode, as shown in FIG. 5B, and a closed mode, as shown in FIG. 5C. The apparatus can be used in either mode depending on whether fluid isolation of the sample from the bulk fluid is desired for the particular data that are being collected. Referring also to FIG. 1B, for example and without limitation, the open mode may be suitable for measuring dissolved oxygen (DO), dissolved carbon dioxide, temperature, pH or cell density while the closed mode is suitable for measuring OUR or nitrification. In either mode, shown in FIGS. 5B and 5C, a sample chamber 46 (indicated by the phantom lines) is defined by a chamber wall 47 of the holder, which will be described below, an interior of the body, and the separator.

Referring again to FIGS. 2A-5C, an exemplary embodiment of the apparatus also includes a holder 33 such as the illustrated holder tube, which houses one or more sensing probes 35 interior to the separator 32. To collect data on the sample, the one or more probes extend into the sample chamber 46 which may or may not be fluidly isolated from the bulk fluid depending on whether it is in the closed or open position. The one or more probes used with the present invention may be a customized probe or any commercially available probe, for example and without limitation, a fluorescence-based optical probe, an electrochemical probe, a dissolved oxygen probe, a dissolved carbon dioxide probe, or a combination of any number thereof. Probes for other metabolites such as glucose, glutamine, glutamate, lactate, or ammonia, and other gases may also be employed.

Figure 4:
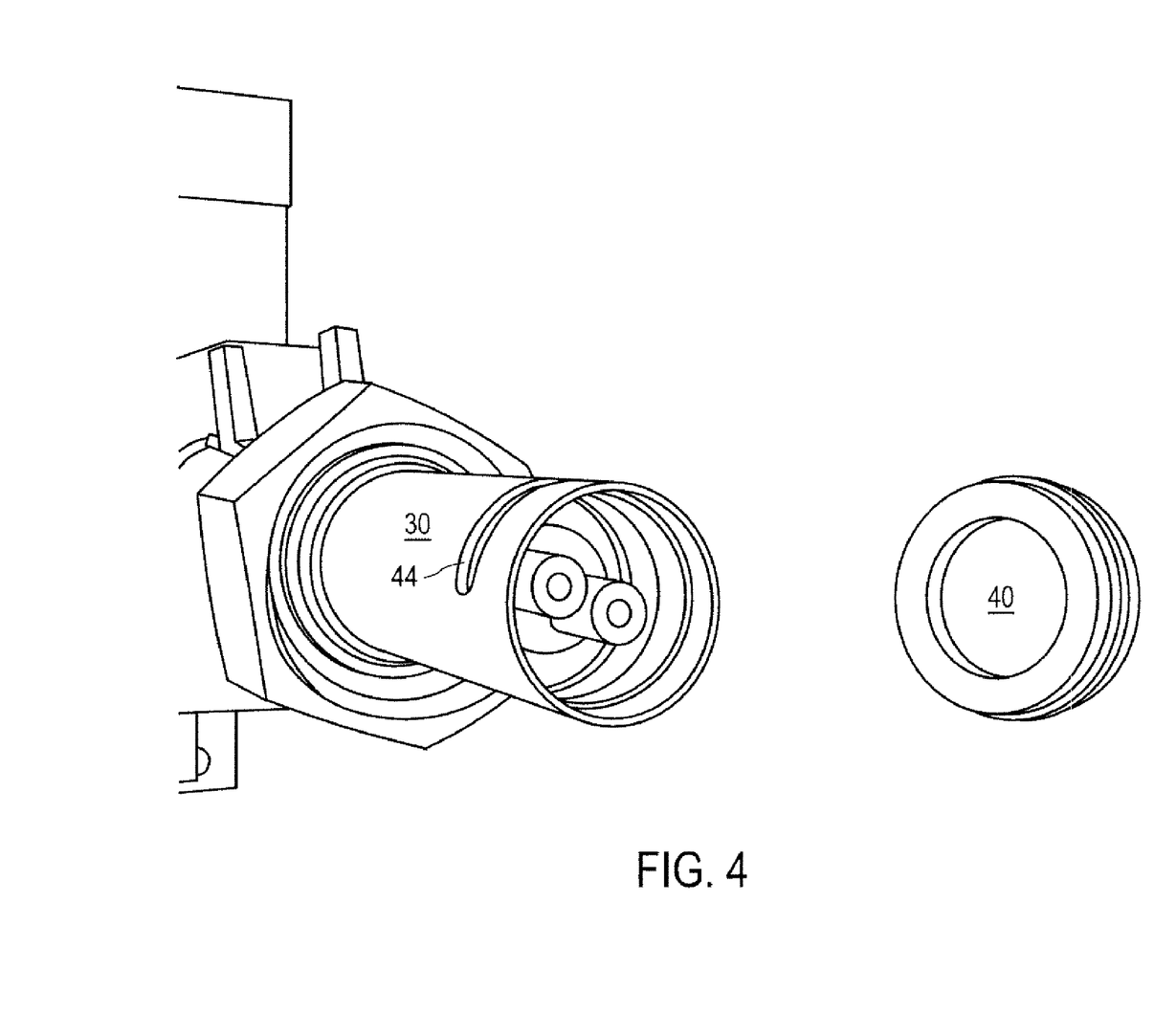
FIG. 4 is a front perspective view of an exemplary embodiment of the present invention.
Figure 6:
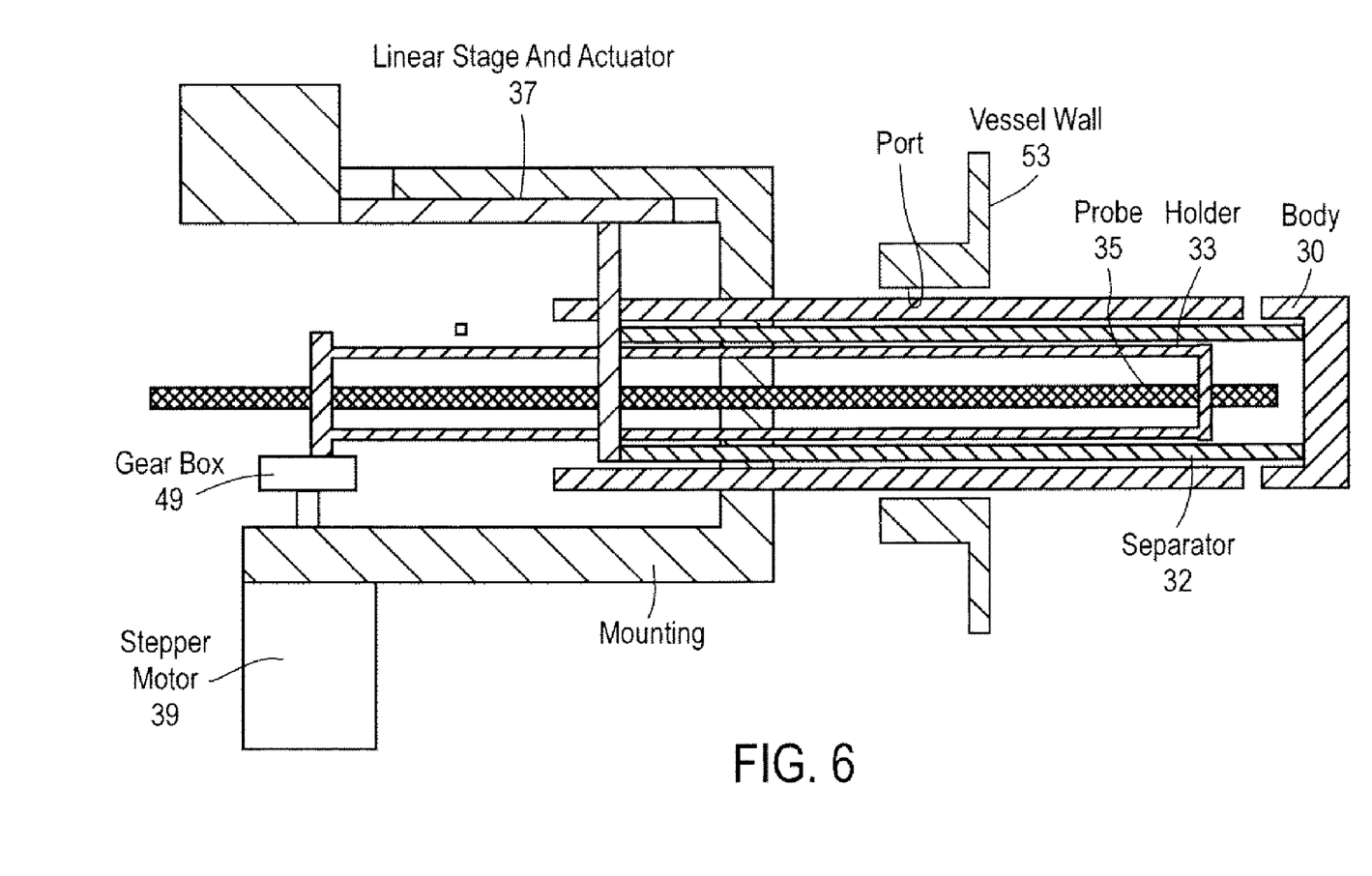
FIG. 6 is a side cross-sectional view of an apparatus of the invention as mounted in a port of a vessel wall and equipped with a linear stage and stepper motor.
Figure 7:
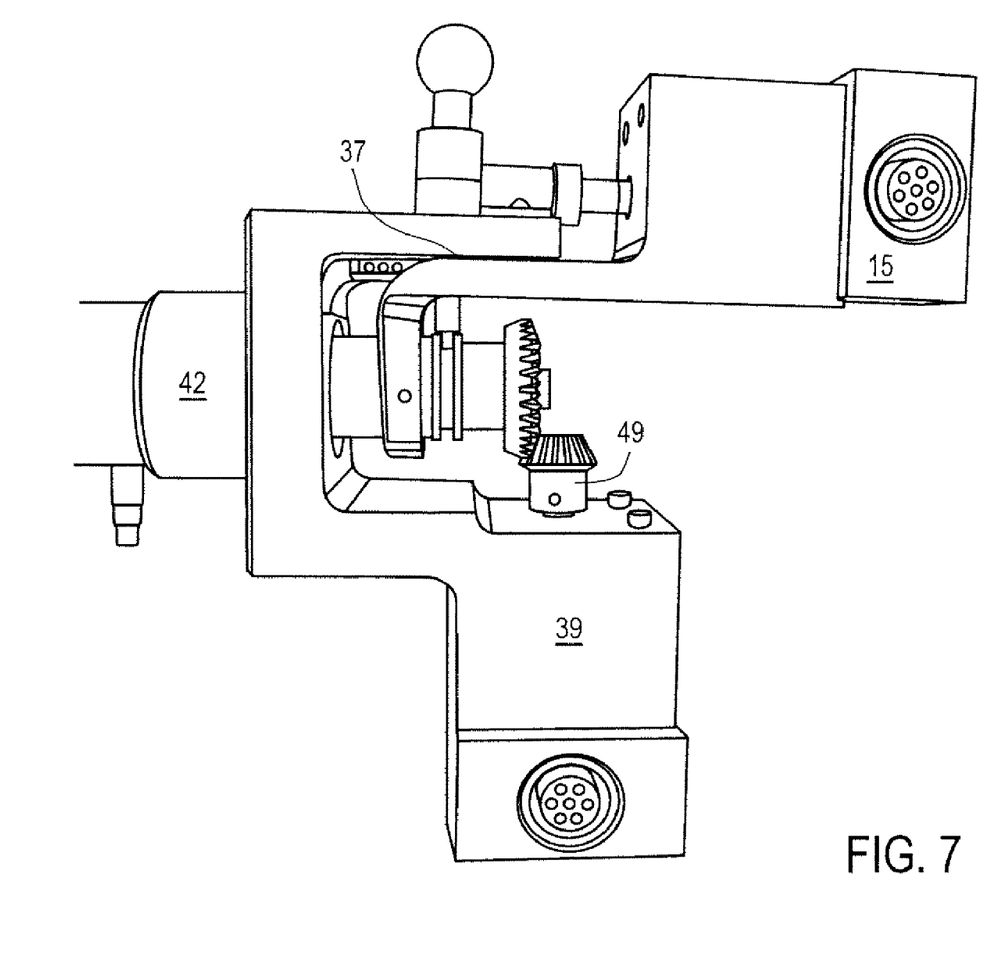
FIG. 7 is an enlarged view of exemplary components used in conjunction with the apparatus of the present invention.

As illustrated in FIGS. 4 and 5A, one or more probes 35 may be mounted off-center with respect to a central axis of the holder, the separator, and/or the body. FIG. 4 illustrates two probes, provided symmetrically around a center. FIG. 5A illustrates a single off-center probe. It should be appreciated by those of ordinary skill in the art that the present invention is not limited to any number or disposition of probes. Referring also to FIG. 6, the body may be connected to a stepper motor 39 and gear box 49, such that the holder is rotatable around a central axis. In the case of the one or more off-center probes, the probe(s) can be used to stir, agitate or otherwise manipulate the sample in the sample chamber. This feature of the invention provides the advantages of keeping cells or other sample components in suspension and prevent gaseous, e.g. $O_2$, $CO_2$, etc. or metabolite concentration gradients from forming. In some embodiments, any number of stirrers such as paddles or the like may be attached to one or more of the probes or otherwise mounted within the sample chamber. It should be appreciated by those of ordinary skill in the art that stirrer(s) may be provided regardless of the number of probes or whether the probes are mounted on- or off-center.

Figure 8A:
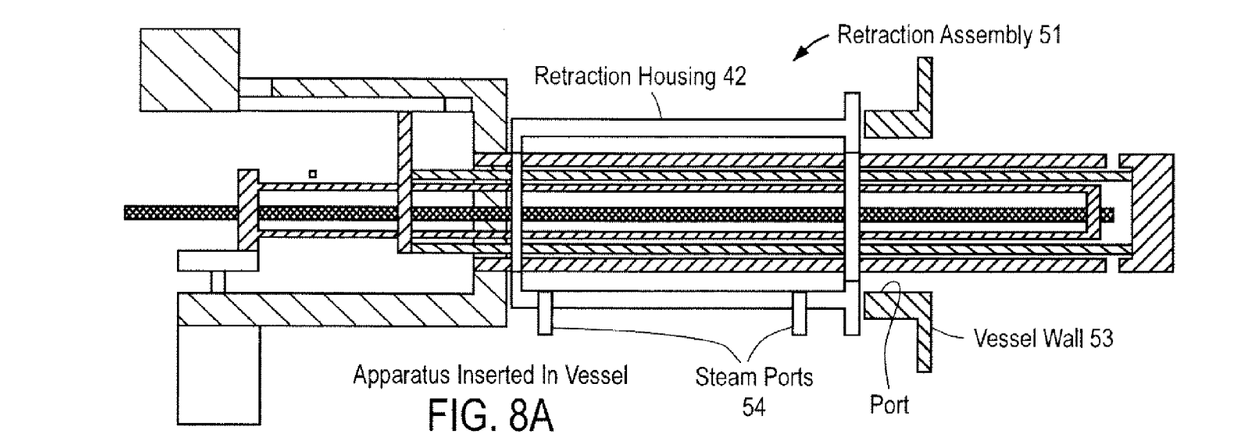
FIG. 8A shows the apparatus mounted in place through a vessel wall and FIG. 8B shows the apparatus retracted from the vessel wall.

In some embodiments, as illustrated in FIGS. 6 and 8, the separator is attached to a linear stage and actuator, which provide the axial movement of the separator between the open position/mode of FIG. 10, and the closed position/mode of FIG. 9. The linear stage may be made of various materials, including without limitation, e.g. steel, non-reactive metals, polymers, etc.

Figure 8B:
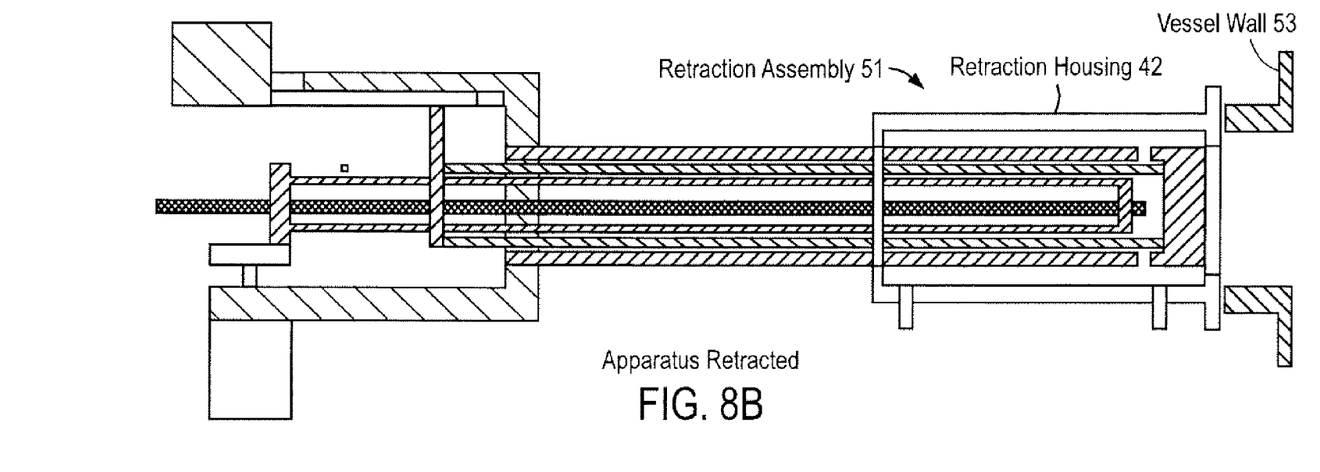
Figure 11:
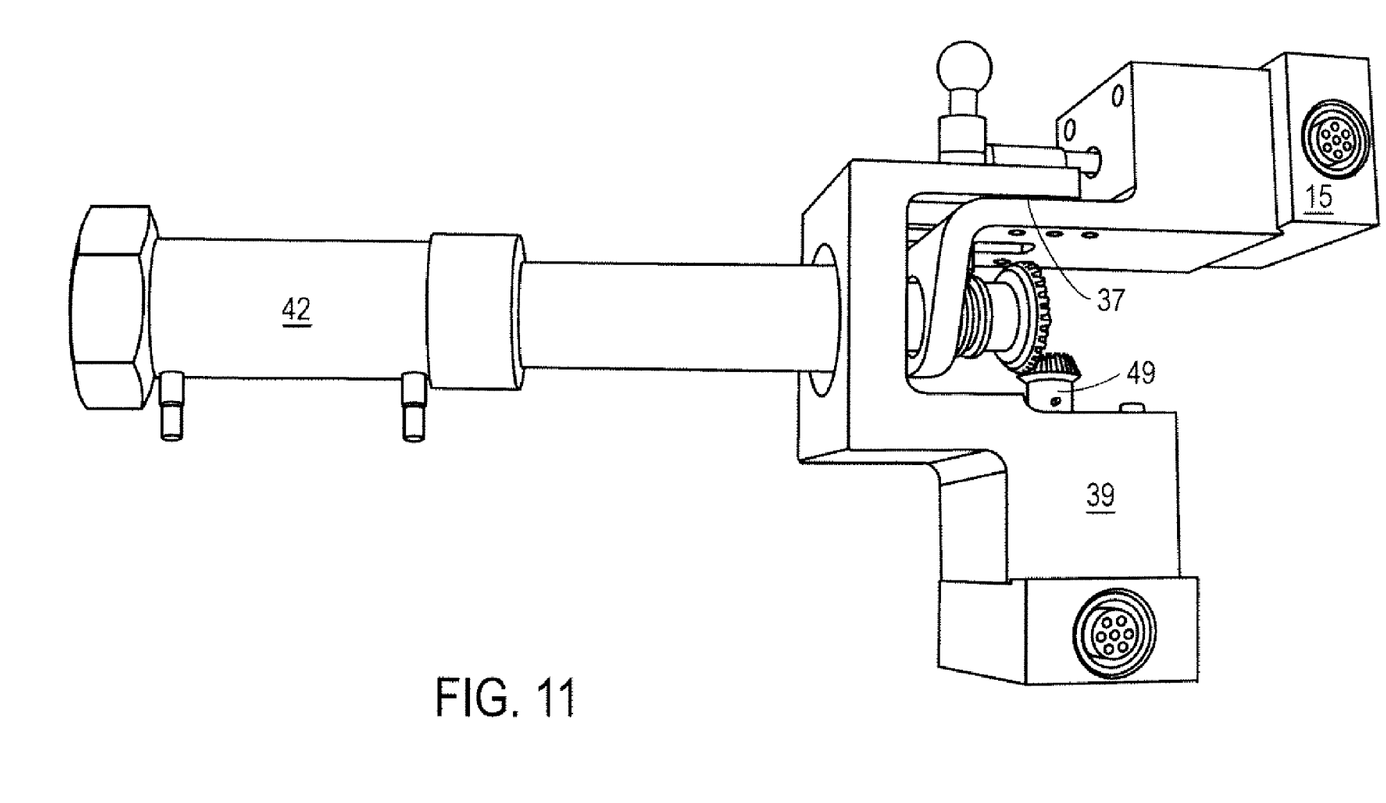
FIG. 11 is an external side view of an apparatus of the invention as it would appear in the process of being retracted.
Figure 12:
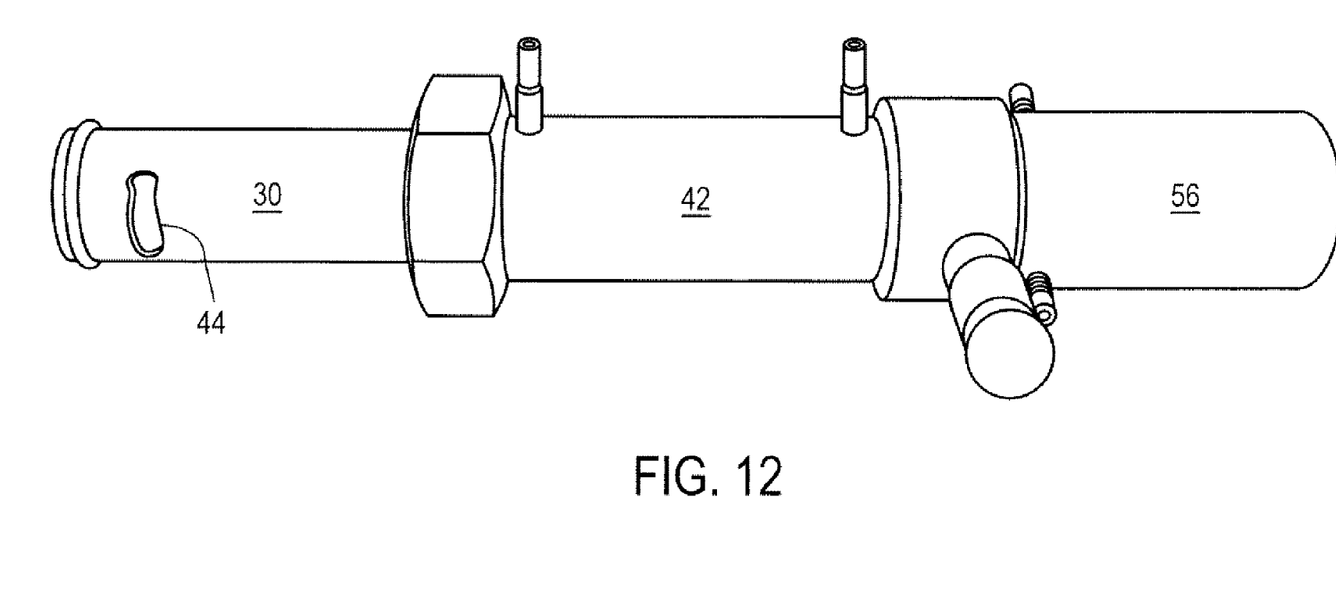
FIG. 12 is an external side view of an apparatus of the invention with an autoclave cap.

Referring now to FIGS. 8B and 11, the inventive apparatus can be adapted for use with a retraction system 51. The retraction system may include the inventive apparatus, a vessel 53 containing the bulk fluid, and a retraction assembly mounted onto the vessel. The retraction assembly includes retraction housing 42, wherein body 30 is configured for removal and sealing insertion through the retraction housing into the bulk fluid. As illustrated in FIG. 9-11, the retraction housing may include one or more steam ports 54, through which steam can be injected for sterilization purposes.

Figure 3:
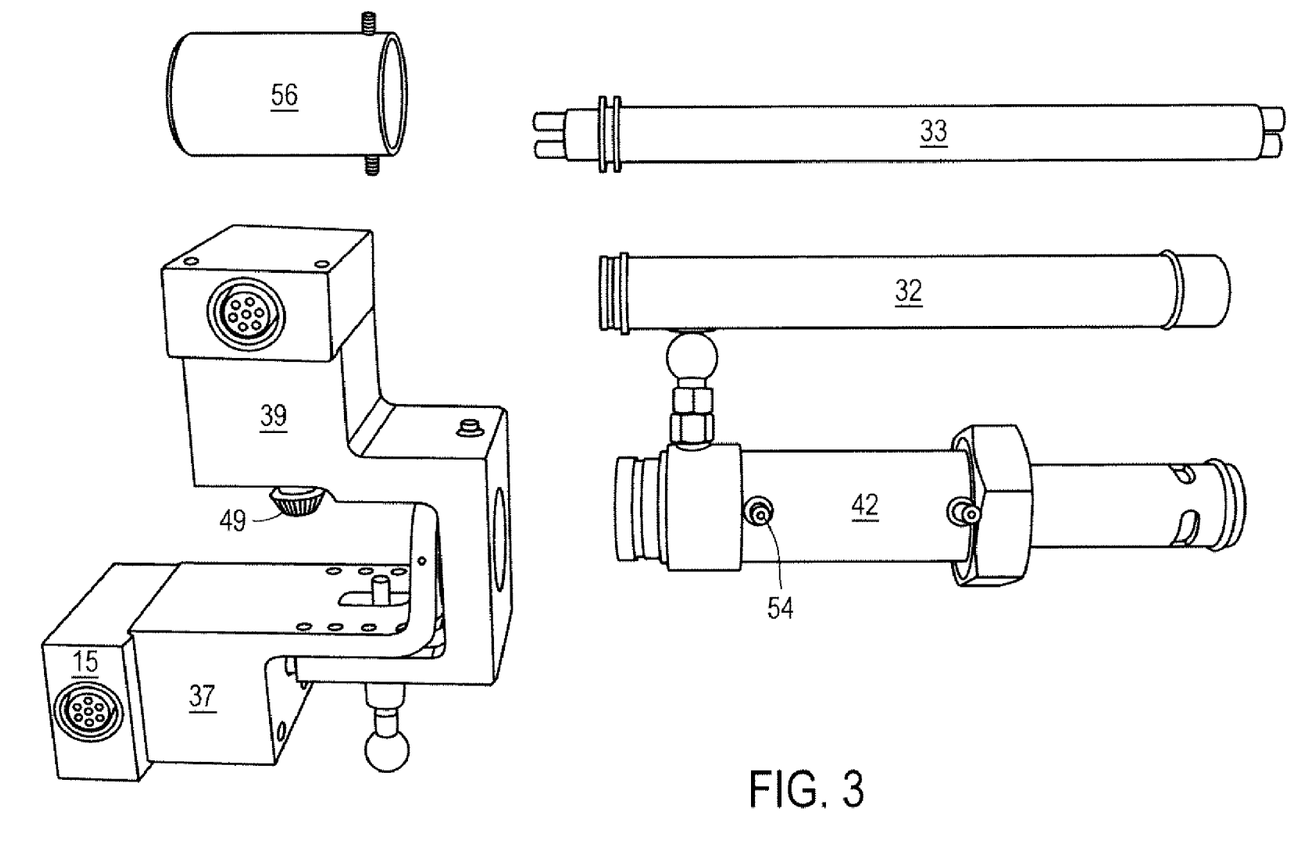
FIG. 3 is an enlarged view of various components of an exemplary embodiment of the present invention.

Referring to FIGS. 3 and 9, in some embodiments, the apparatus is detachable from the linear stage and actuator and stepper motor and gear box or any other mechanism by which movement of the separator and holder is achieved, leaving an exposed opening on one end of the apparatus. An autoclave cap 56 can then be placed on the exposed end of the apparatus for autoclaving or sterilize-in-place (SIP) procedures. In some embodiments, the cap can be placed on the body on a portion distal from the apertures. The cap may be made of steel, glass or any other material known in the art for its heat or pressure-resistance.

Any custom or commercially available retraction assembly can be used, including but not limited to, the Mettler Toledo InTrac® retraction assembly and others known in the art. The adaptability of the present invention for use with a retraction system is particularly advantageous for long-term perfusion processes that typically run for durations of three months or longer. The retraction aspect of the invention allows for swapping, adjustment, maintenance or replacement of probes, e.g. to remove defective/broken probes or test for a different parameter of the sample, without significant process interruption.

In some embodiments, the apparatus may include one or more O-rings to provide a mechanical or fluidic seal at any interface between two or more components of the invention. An O-ring can be positioned between end cap 40 and body 30, between separator 32 and the end of body 30 proximal to aperture(s) 44, or between separator 32 and holder 33.

Although the body, separator, holder, and one or more probes are illustrated in the accompanying drawings as tubular structures, those of ordinary skill in the art should recognize that these components may take any shape or form as can their cross-sections, e.g. regular: elliptical, circular, polygonal, etc. or irregular.

In use, the apparatus is inserted into a bulk fluid such as a culturing media in a bioreactor. In the illustrated embodiment, the apparatus is inserted through a port of the reactor or vessel wall, however, one will appreciate that the apparatus may be configured for insertion directly into a bulk fluid such as a river, lake or marsh, aquatic culture tanks, agricultural water supplies and seawater. After insertion into the bulk fluid, the separator can be placed in either the open position (FIG. 5B) or closed position (FIG. 5C). When the separator is in the open position, a portion of the bulk fluid will flow through the apertures into the sample chamber, allowing measurement of parameters such as pH, temperature, dissolved oxygen, etc. in the bulk fluid. For some uses, the data is collected while the separator is in the closed position, thereby fluidly isolating a sample in the sample chamber from the bulk fluid. The data collected by the probes in the closed mode may be suitable for assessing the physiological state of cells in the reactor and measuring parameters such as nitrification or oxygen uptake rate of culturing cells.

The present invention has a number of applications, including the use of a dissolved carbon dioxide probe and dissolved oxygen probe, simultaneously or in turn, to determine the respiratory quotient of cells in culture. The dissolved carbon dioxide probe measures $pCO_2$ over time to calculate the carbon dioxide evolution rate (CER). The CER can then be employed in conjunction with the OUR determined by the dissolved oxygen probe to determine the respiratory quotient (RQ).

The invention can also be used for monitoring cell health and physiological states in culture. For instance, cell density should remain relatively constant in processes run in steady-state. The oxygen consumption rate should likewise remain constant. Under such conditions, a detected flux in the oxygen consumption rate can signal an unexpected or undesired change in cell density and thereby allow correction measures to be taken. Under other conditions, where a change in cell density is expected, a detected stasis in cell density by OUR measurement might be an indication of other problems and warrant a more thorough investigation of the cause. Since the apparatus of the invention has an open mode, it can be used as an enhanced sensor in reactors for mammalian cell culture, prokaryotic and eukaryotic fermentation, aquatic systems, ecological studies, or any other contexts.

EXAMPLE

The following is offered to illustrate the operation of an embodiment of the present invention and not by way of limitation.

Experimental: Appropriate probes were selected and installed in the system, the condition of all O-rings and parts checked and the autoclave cap attached to the system, which was processed in the autoclave. After autoclaving, the autoclave cap was removed from the apparatus and a motor mount installed in its place. The apparatus was then installed onto a vessel/fermentor along with additional control equipment as needed (pH probes, temperature probes, etc.). Probe(s) were connected to the appropriate transmitters, i.e. the DO transmitter, and their signals sent to a data acquisition or SCADA system (FermWorks™ 2.1 by Jova Solutions, San Francisco). Stepper motors that move the probes and the separator were connected to a stepper motor controller (2× TIMS 0201™, Jova Solutions, San Francisco) and the control software initialized. In the setup, TIMS 0201 was connected via USB to the process control computer running the fermentor and the control program in a plug-in for FermWorks™.

The appropriate parameters for system operation were set. These parameters included oscillation/mixing frequency, open and closed position of the separator, measurement frequency (in number of measurements per hour in auto mode). The DO probes of the system were then calibrated, 0% and 100% air saturation being achieved by respectively sparging the reactor with nitrogen and air. Fermentation procedures were performed: adding the medium and cells to the reactor and starting the SCADA control loops for critical parameters, including dissolved oxygen (DO), pH, temperature, and agitation. Parameters/conditions were allowed to stabilize before measurement in the closed mode to avoid otherwise skewed readings. Measurement in closed mode was initiated by moving the separator and closing the sample chamber via the control program. Sample mixing was implemented by the stepper motor control software, causing the probe holder to spin clockwise or counterclockwise as desired and turn the probe(s). Changes in probe signals, e.g. oxygen consumption, were recorded over time.

The sample chamber was opened and the sample released back into the bulk fluid once the probe signal reaches a predetermined threshold. Rotation of the holder was ceased and the probe(s) readings allowed to stabilize before another measurement was taken. Additional measurements were timed by the control software. The oxygen uptake rate was calculated from the oxygen consumption over time as measured relative to the actual cell density.

Figure 13:
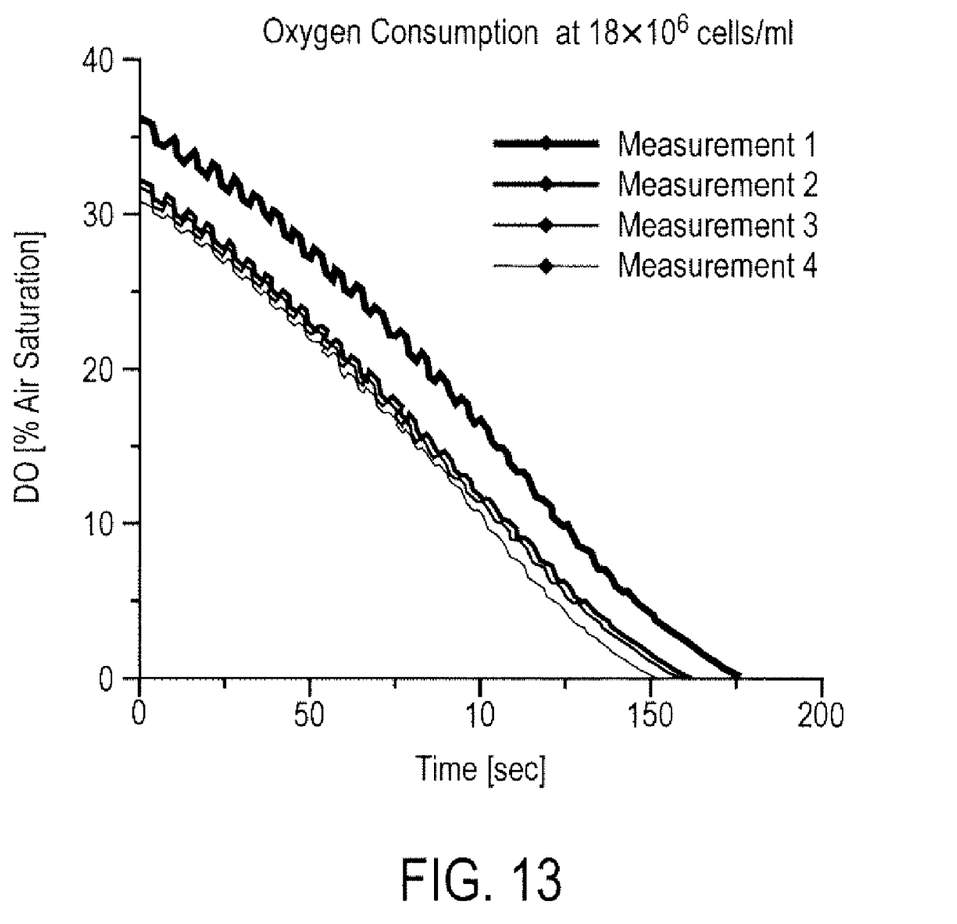
FIG. 13 is a graph of four oxygen uptake rate measurements taken during the perfusion process at a cell density of $18 \times 10^6$ cells/mL.

All measurements were taken during a four-week period of a perfusion process, the conditions of which are provided in Table 1. The results plotted in FIG. 13 show good reproducibility of measurements by the present invention. Table 2 shows the calculated OURs as measured on thirteen days during the test period and the relative error associated with each measurement. The average relative error is 5.5%.

For comparison, the global mass balancing (GMB) method known in the art was used to estimate the OUR for one of the experiments at a cell density of $15.5 \times 10^6$ cells/mL. The GMB method resulted in an estimated OUR of about 2.2 pmol/cell·d as compared to an OUR of about 2.0 pmol/cell·d measured by the in situ apparatus of the present invention.

TABLE 1

| Parameter | Value |
| --- | --- |
| pH | 6.8 |
| Temperature | 35.5 |
| DO | 50% |
| Medium | Protein-free |
| Cell Line | Baby Hamster Kidney (BHK) |
| Cell Specific Perfusion Rate (CSPR) | variable |
| Cell Density | $3\text{-}20 \times 10^6$ cells/mL |

TABLE 2

| Cell Density $1 \times 10e^6$ cells/mL | CSPR condition | OUR (pmol/cell · d) | Error (%) | Datasets |
| --- | --- | --- | --- | --- |
| 3.26 | B | 2.7 | 6.7 | 2 |
| 9.55 | C | 2.47 | 1.6 | 4 |
| 10.3 | A | 3.14 | 4.7 | 4 |
| 11.17 | A | 2.74 | 4.7 | 4 |
| 12.13 | A | 2.81 | 2.5 | 2 |
| 13.46 | A | 2.51 | 10.8 | 3 |
| 13.58 | A | 2.45 | 6.5 | 4 |
| 13.76 | A | 3.9 | 4.6 | 3 |
| 15.26 | B | 2.17 | 0.0 | 2 |
| 15.5 | B | 2 | 9.5 | 4 |
| 17.11 | C | 2.64 | 14.4 | 3 |
| 17.77 | B | 2.14 | 3.0 | 5 |
| 20.2 | A | 2.28 | 3.5 | 2 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for in situ measurements comprising:
    a body configured for insertion into a bulk fluid, said body including an interior and one or more apertures for fluid communication between the interior and the bulk fluid;
    a separator received in the body interior, said separator being movable between an open position remote from said one or more apertures and a closed position adjacent said one or more apertures;
    a holder mounted within the separator and including a chamber wall, the chamber wall, the separator, and the body interior defining a sample chamber; and
    one or more probes received by the holder and including a respective probe end that extends into the sample chamber.

2. The apparatus of claim 1, wherein the sample chamber is in fluid communication with the bulk fluid when the separator is in the open position, and fluidly sealed from the bulk fluid when the separator is in the closed position.

3. The apparatus of claim 1, wherein said one or more apertures are configured so as to permit free flow of the bulk fluid around the one or more probe ends when the separator is in the open position and to prevent free flow of the bulk fluid when the separator is in the closed position.

4. The apparatus of claim 1 wherein at least one of said one or more probes is mounted off-center with respect to the holder.

5. The apparatus of claim 1 further comprising one or more stirrers within the chamber for stirring fluid within the sample chamber.

6. The apparatus of claim 1, wherein the holder is rotatably mounted within the separator such that said at least one off-center probe end rotates within the sample chamber thereby forming said at least one of said one or more stirrers.

7. The apparatus of claim 1, wherein at least one of said one or more probes is a fluorescence-based optical probe.

8. The apparatus of claim 1, wherein at least one of said one or more probes is an electrochemical probe.

9. The apparatus of claim 1, wherein one of said one or more probes is a dissolved oxygen probe.

10. The apparatus of claim 1, wherein one of said one or more probes is a carbon dioxide probe.

11. The apparatus of claim 1, wherein said body is configured for insertion into a port of a bioreactor comprising said bulk fluid.

12. A system for in situ measurements comprising:
the apparatus of claim 1;
a vessel containing the bulk fluid; and
a retraction assembly mounted on said vessel.

13. The system of claim 12, wherein the retraction assembly includes a retraction housing, and wherein the body is configured for removable and sealing insertion through the retraction housing into the bulk fluid.

14. The system of claim 12, wherein the retraction housing includes one or more steam ports for conducting steam.

15. The system of claim 13, wherein the retraction housing includes one or more steam ports for conducting steam.

16. The system of claim 12, further including an autoclave cap over an end of the retraction housing.

17. A method of performing in situ measurements comprising:
contacting the body of the apparatus of claim 1 with the bulk fluid when the separator is in the open position;
measuring one or more parameters of the bulk fluid using said one or more probes.

18. The method of claim 17, wherein the bulk fluid is in a bioreactor.

19. The method of claim 17, wherein said one or more parameters include a measure of dissolved oxygen in the bulk fluid.

20. The method of claim 18, wherein said one or more parameters include a measure of dissolved oxygen in the bulk fluid.

21. A method of performing in situ measurements comprising:
contacting the body of the apparatus of claim 1 with the bulk fluid when the separator is in the open position;
isolating a sample of the bulk fluid in the sample chamber by moving the separator to the closed position; and
measuring one or more parameters of the sample using said one or more probes.

22. The method of any of claim 21, wherein the bulk fluid is in a bioreactor.

23. The method of claim 21, wherein the sample comprises cells and at least one of said one or more parameters is indicative of a physiological state of the cells.

24. The method of claim 22, wherein the sample comprises cells and at least one of said one or more parameters is indicative of a physiological state of the cells.

25. The method of claim 23, wherein said one or more parameters include oxygen uptake rate of the cells.

26. The method of claim 21, further comprising, after the contacting step:
rotating the holder around an axis to stir the sample.

27. A method of performing in situ measurements comprising:
contacting the body of the apparatus in the system of claim 12 with the bulk fluid when the separator is in the open position;
measuring one or more parameters of the bulk fluid using said one or more probes.

28. The method of claim 27, wherein the bulk fluid is in a bioreactor.

29. A method of performing in situ measurements comprising:
contacting the body of the apparatus in the system of claim 12 with the bulk fluid when the separator is in the open position;
isolating a sample of the bulk fluid in the sample chamber by moving the separator to the closed position; and
measuring one or more parameters of the sample using said one or more probes.

30. The method of claim 29, wherein the bulk fluid is in a bioreactor.

31. The method of claim 29, wherein the sample comprises cells and at least one of said one or more parameters is indicative of a physiological state of the cells.

32. The method of claim 30, wherein the sample comprises cells and at least one of said one or more parameters is indicative of a physiological state of the cells.

33. The method of claim 31, wherein said one or more parameters include oxygen uptake rate of the cells.

34. The method of claim 29, further comprising, after the contacting step:
rotating the holder around an axis to stir the sample.

\* \* \* \* \*